United States Patent [19]
Partin et al.

[11] Patent Number: 5,082,630
[45] Date of Patent: Jan. 21, 1992

[54] FIBER OPTIC DETECTOR FOR IMMUNO-TESTING

[75] Inventors: Judy K. Partin; Thomas E. Ward; Alan E. Grey, all of Idaho Falls, Id.

[73] Assignee: The United States of America as represented by the United States Department of Energy, Washington, D.C.

[21] Appl. No.: 516,590

[22] Filed: Apr. 30, 1990

[51] Int. Cl.⁵ .............................................. G01N 21/17
[52] U.S. Cl. .................................. 422/83; 422/82.08; 356/437; 356/38; 436/518; 436/527
[58] Field of Search .......................... 422/82.05–82.08, 422/82.11, 83, 84, 85, 86, 88; 436/518, 527, 546, 800, 900, 901; 356/317, 318, 417, 38, 437; 128/634

[56] References Cited
U.S. PATENT DOCUMENTS

| | | | |
|---|---|---|---|
| 3,998,591 | 12/1976 | Eckfeldt | 422/91 |
| 4,003,707 | 1/1977 | Lübbers et al. | 356/318 |
| 4,050,895 | 9/1977 | Hardy et al. | 422/86 |
| 4,264,209 | 4/1981 | Brewster | 356/437 |
| 4,353,886 | 10/1982 | Lukens et al. | 422/83 |
| 4,558,014 | 12/1985 | Hirschfeld et al. | 422/61 |

Primary Examiner—Sam Rosen
Assistant Examiner—Christopher L. Chin
Attorney, Agent, or Firm—James W. Weinberger; Thomas G. Anderson; William R. Moser

[57] ABSTRACT

A portable fiber optic detector that senses the presence of specific target chemicals in air or a gas by exchanging the target chemical for a fluorescently-tagged antigen that is bound to an antibody which is in turn attached to an optical fiber. Replacing the fluorescently-tagged antigen reduces the fluorescence so that a photon sensing detector records the reduced light level and activates an appropriate alarm or indicator.

14 Claims, 3 Drawing Sheets

FIBER OPTIC DETECTOR FOR IMMUNO-TESTING

CONTRACTUAL ORIGIN OF THE INVENTION

The U.S. Government has rights in this invention pursuant to Contract No. DE-AC07-76ID01570 between the U.S. Department of Energy and EG&G Idaho, Inc.

BACKGROUND OF THE INVENTION

This invention relates to a compact and portable detection device for specific chemical compounds, such as hazardous chemicals or illegal drugs, for example heroin, cocaine or marijuana. The portable device can be conveniently carried by an individual, is extremely sensitive to the compound being detected, and is minimally affected by potential interfering substances.

The device of the present invention is based upon the use of fiber optic spectroscopy. Sensors to detect light emitted from an optical fiber can be constructed that are sensitive, compact, readily portable, and require a minimum of training for their use. The preferred process of the invention relies upon a biological system, and optical and electronic components to monitor a decrease in fluorescence when a subject molecule (such as a drug) displaces a fluorescently-tagged drug derivative (antigen) from an antibody specific for that drug.

Fluorescence occurs when an atom or molecule emits visible radiation when passing from a higher to a lower electronic state. The term is restricted to phenomena in which the time interval between absorption and emission of energy is relatively short ($10^{-8}$ to $10^{-3}$ second), thus distinguishing fluorescence from phosphorescence, wherein the time interval may extend to several hours. Fluorescent materials may be liquid or solid, organic or inorganic. Fluorescent crystals such as zinc or cadmium sulfide are used in lamp tubes, television screens, scintillation counters, and similar devices. Fluorescent dyes are used for labeling molecules in biochemical research.

Illicit drug traffic throughout the world has been steadily rising. It is estimated that in 1985, over 150 metric tons of cocaine and approximately 6 metric tons of heroin were smuggled into the United States alone. It is also estimated that less than 4% of these drugs were detected and confiscated as they crossed our borders even though current interdiction methodology has improved. During 1987, 27 thousand pounds of drugs were confiscated; during 1988, 38 thousand pounds; and in the first few months of 1989, 10 thousand pounds. However, methods and techniques for smuggling drugs have also improved, and it is a certainty that only a small percentage of the drugs entering this country are confiscated. It is speculated that a high percentage of the drugs entering this country are concealed in enclosed spaces, such as cargo containers. On average, approximately 15 manhours are required to thoroughly search a cargo container, so that less than 3% of the 8 million cargo containers entering the United States each year are inspected. Because of the vast number of cargo containers and enclosed boxes of every description, a method for rapid inspection and detection is required One reason for the low rate of drug interdiction is the lack of adequate instrumentation available to field agents. Most of the instruments currently available, such as mass spectrometers and gas chromatographs are not portable, require 100/220V power, and must be operated by well-trained technicians. Therefore, instrumentation is needed that is readily portable, operable with a minimum of training, capable of detecting the compounds of interest at extremely low concentration, minimally affected by interfering substances, rugged, and completely user friendly.

While the apparatus and process of the present invention are initially intended to detect illegal drugs, the invention is equally applicable for detection of a wide range of chemical compounds, limited only by the biological and tagging procedures set forth below. Therefore, the invention should not be considered as limited solely to the detection of drugs. For example, the methods described herein can be used in business or industrial environments to detect the presence of certain hazardous chemicals likely to be found in such environments.

Cocaine and heroin vapors in the air are typically detected with mass spectrometry and GC-MS. However, the "stickiness" of the drug molecules and their extremely low vapor pressures present measurement problems. The drug molecules tend to adhere to tubing walls instead of entering the detection chamber. Because of the drugs' low vapor pressures, concentration is required for detection. This typically consists of passing a large volume of air through tubing or a filtering system and then liberating the attached drug molecules with heat.

Another method of detecting illegal drugs is described in U.S. Pat. No. 4,353,886, issued Oct. 12, 1982. This patent discloses the vapor deposition of indium onto a glass slide which is then coated with an antibody specific for a given drug. Since indium functions as a Lewis acid (an electron acceptor) the non-antigen binding end of the antibody, with a high amine concentration, preferentially attaches to the indium metal. The antigen binding end is therefore free to combine with any drug (or antigen) molecules in the air. After exposure to the drug, the test plate can be read either by visual observation of cloudiness or by fluorescence measurement. Drugs with a vapor pressure of $1 \times 10^{-9}$ Torr can be detected with a one- to two-minute exposure of the test plate.

SUMMARY OF THE INVENTION

In its most basic embodiment, the present invention functions by attachment of antibodies to the distal end of an optical fiber or waveguide and saturating the antibodies with a fluorescently-tagged antigen. When exposed to an air sample, a decrease in fluorescence indicates the presence of the suspect chemical compound in the air sample. The specificity of antibody-antigen reactions results from their complimentary configuration. Certain functional groups, on the antigen such as polar and quaternary ammonium groups, seem to bind with corresponding complementary structures in the antibody molecule. The fluorescently-tagged antigen is displaced by the airborne compound specific for that antibody, and the detecting diode monitors the decrease in fluorescence resulting from this displacement.

Cocaine and heroin both contain a tertiary amine as the primary active site, and have the following structures:

Cocaine

Heroin

In addition to the tertiary amine, heroin also contains two acetyl esters, while cocaine has one methyl ester. However, cocaine is frequently transported as a sulfate salt, which effectively deactivates the tertiary amine and causes a decrease in vapor pressure.

The vapor pressures of cocaine and heroin are extremely low, making detection difficult. The calculated vapor pressures and concentrations of vapors in air, as a function of temperature, are shown in the following tables:

| Temperature | | Vapor Pressure | Concentration |
|---|---|---|---|
| C° | F° | Atmospheres | in Air |
| COCAINE | | | |
| 20 | 68 | $1.14 \times 10^{-10}$ | 114 ppt |
| 30 | 86 | $5.25 \times 10^{-10}$ | 525 ppt |
| 40 | 104 | $2.19 \times 10^{-9}$ | 2 ppb |
| 50 | 122 | $8.37 \times 10^{-9}$ | 8 ppb |
| HEROIN | | | |
| 20 | 68 | $3.59 \times 10^{-13}$ | 359 ppq |
| 30 | 86 | $2.54 \times 10^{-12}$ | 3 ppt |
| 40 | 104 | $1.59 \times 10^{-11}$ | 16 ppt |
| 50 | 122 | $8.86 \times 10^{-11}$ | 89 ppt |

Such concentrations are below the reliable detection limit of most analytical instrumentation. In the process of the present invention, this is overcome by installing a vacuum system to draw a large volume of air over the optical fiber. The optical fiber, in turn, acts as a concentrator, in the same manner as glass tubing or a filter. This technique brings the drug concentration into the detection range of the inventive apparatus.

Antibody preparations against a particular drug can be made by attaching the smaller drug molecule to larger carrier molecules, such as albumin, and injecting the resulting combination into an antibody-producing host animal, such as a mouse, rabbit, or goat. In the case of rabbits or goats, the antibodies can be prepared in large amounts, but they will be heterogeneous (polyclonal). In the case of mice, homogeneous (monoclonal) antibodies can be produced, and with sufficient resources, relatively large amounts can be prepared. Albumin is used in conjunction with low molecular weight (smaller) drug molecules since mammals typically do not have the capacity to manufacture antibodies for the smaller, low molecular weight molecules such as cocaine and heroin. For example, the molecular weight of cocaine is about 300, while that of serum albumin is about 60,000.

Antibodies bind to antigens using the "front end" (the $F_{ab}$ region) of the antibody molecule. A number of biological molecules interact specifically with the "back end" (the $F_c$ region) of the antibody. Exemplary of these biological molecules is Protein A from *Staphylococcus aureus*. Instead of binding antibodies directly to a derivatized optical fiber, which might well lead to a high proportion of inactive antibody molecules because of random attachment, it is possible to coat the fiber with, for example, Protein A, and then allow the antibody to bind with the Protein A under native conditions, possibly followed by covalent attachment of the antibody. This produces a fiber on which most of the antibody molecules are oriented with their $F_{ab}$ regions pointing away from the fiber, ready to interact with the drug. Proteins can be attached to the fiber using chemical reagents, after derivatizing the fiber with aminopropyl or carboxypropyl groups. Alternatively, the fiber can be covalently coated with a polyamine before attachment of the Protein A.

In order to detect the binding of the drug to the antibody, it is possible to use the technique of fluorescently-tagged antigen preloading. When light travels through an optical fiber, a certain percentage can escape and interact with the coating surrounding the fiber. If the fiber is coated with a fluorescing compound, and if the wavelength of the light matches the excitation characteristics of the fluorescent coating molecules (including any such molecules bound to the antibodies attached to the fiber), these molecules will fluoresce. In practice, an antibody-coated fiber is saturated with a fluorescently-tagged drug derivative (antigen), and the fiber is then exposed to an airborn sample of the drug to be detected. If the drug is present, the airborn drug molecules displace some of the bound, fluorescently-tagged derivative, resulting in a decrease in the fluorescent signal. The extent of the decrease is proportional to the concentration of drug molecules in the surrounding environment.

It is critical that the fluorescently-tagged drug derivative be properly chosen. First, the fluorescent tag must have good absorption and fluorescent yield characteristics, which provide high sensitivity. Second, it must absorb at wavelengths which can be conveniently used in fiber optic systems. Fluorescein ($C_{22}H_{12}O_5$) and rhodamine ($C_{28}H_{31}ClN_2O_3$) are commonly used as fluorescent tags, and meet these criteria. Fluorescein is an orange-red, crystalline powder which exhibits intense, greenish-yellow fluorescence in dilute alkaline solutions. Rhodamine is a basic red dye, structurally related to xanthene, which forms a bluish red, fluorescent solution. Attachment of the fluorescent tags to the antigen molecules requires a reactive site on the antigen molecule and must not interfere with the binding of the antigen to the drug antibody. The fluorescent tag is attached to the antigen at the same position on the drug which is used to attach it to the carrier for antibody production. The antibodies are directed mostly at the other portions of the drug molecule that protrude away from the carrier, and thus attachment of the fluorescent tag at this position will generally not interfere with antibody binding. The fact that the carrier was attached to the drug at that position also means that there is a reactive atom on the drug (antigen) to which the fluorescent tag ca be attached.

DETAILED DESCRIPTION OF THE INVENTION

Figure 1:
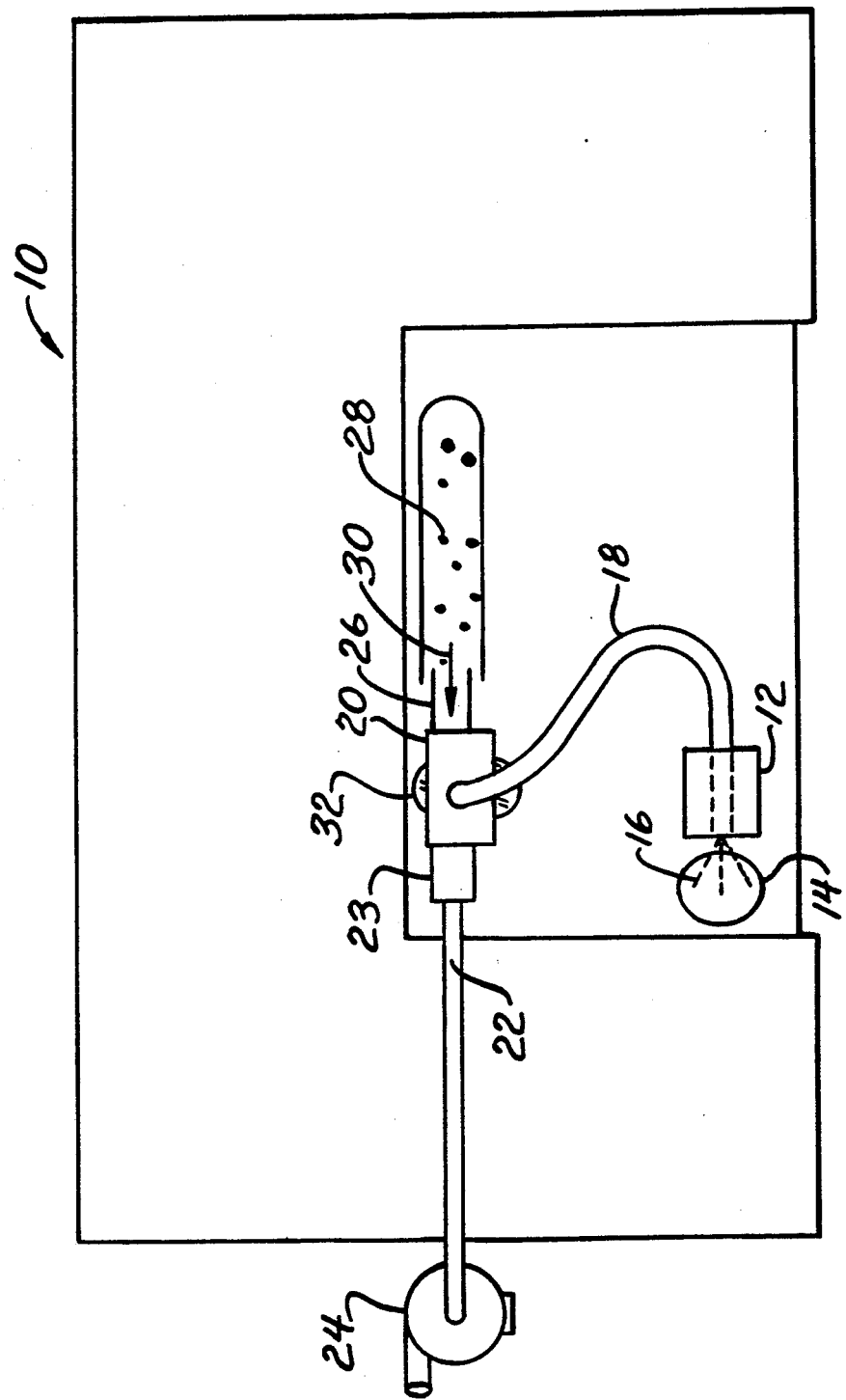
FIG. 1 is a schematic representation of a modified fluorimeter useful in the present invention.

Referring to FIG. 1, the process of the present invention has been confirmed using a Perkin-Elmer Model 512 Fluorimeter 10. This fluorimeter 10 can be modified with means 12 to position the optical fiber 18 in front of a focusing lens 14 to focus the input beam 16 through fiber 18. The fiber 18 provides the optical path to transmit the light to an end of the fiber coated with antibodies. A chamber 20 positions the coated end of the fiber 18 in front of the detector as described below. At least two ports are machined into the holder 20 on either side of the optical fiber 18. A first port 23 is affixed through conduit 22 to a vacuum pump 24 to pull sample air over the fiber. A second port 26 permits the sample air containing drug molecules 28 to enter the chamber 20 as at 30 and contact the antibody-coated fiber.

Airborne drug molecules 28 pass over the coated exposed tip of fiber 18 and replace the drug derivative coated onto the fiber. This reduces the fluorescent light intensity within chamber 20. Light intensity is monitored by a spectrometer through window 32.

Figure 2:
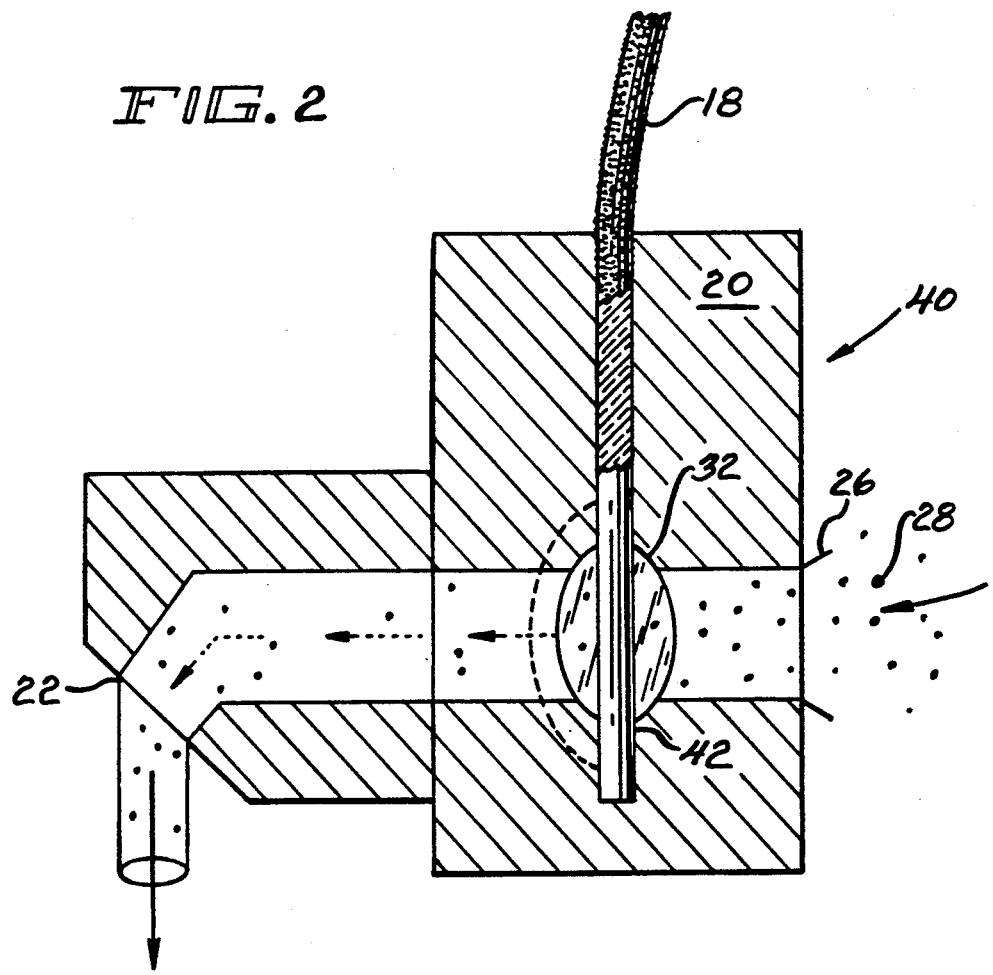
FIG. 2 is a schematic detail of the sensor portion of the fluorimeter.

Referring now to FIG. 2, the enlarged sensor assembly 40 comprises a sensitized and coated distal tip portion 42 of optical fiber 18. While the length of this distal tip portion 42 depends upon the particular devise utilized, the length used by applicants is about one to two centimeters. While the fiber is conventionally jacketed, the distal tip portion 42 is unjacketed and covered by the bonding agents and drug derivative. A reactive chemical such as 3-aminopropyltrimethoxysilane (silane) is preferred, for use as an adhesion promoter that bonds the protein to the optical fiber. The protein coated fiber is then dipped into a solution containing the antibody, with the fiber coating then combining with the non-reactive "back ends" of the antibody molecules. The proper coating produces a fiber tip 42 having the reactive side or "front end" of the antibody facing away from the fiber. Alternate bonding agents include 3-aminopropyltriethoxysilane and 3-carboxypropyltrimethoxysilane. While it is also believed that the bonding method set forth above will produce a fiber having the desired characteristics, it is believed that an antibody can be attached to the fiber by a coating process wherein a polymeric coating having the antibody imbedded therein is applied to the fiber. This method is less desirable because the random orientation of antibodies can result in a portion of the antibody molecules being oriented with their active ($F_{ab}$) sites either imbedded in the polymer or otherwise oriented in a manner so as to not be available for attachment by antigens or drug molecules.

The final step in the preparation of the fiber tip 42 is to immerse the tip portion 42 in the derivatized (fluorescently-tagged) antigen in order to saturate the active areas ($F_{ab}$) of the antibody with the tagged antigen. In a preferred embodiment, fluorescence results from fluorescein molecules attached to the antigen which can be activated by a specific light wavelength at about 490 nm.

The fluorescence of the tagged antigen is excited by light transmitted through the fiber and subsequently detected by light monitoring means, such as a spectroscope, through window 32, as in FIG. 2. When the particular drug molecules that correspond to the antigen enter the chamber 20, the airborn drug molecules displace the fluorescent antigens and attach themselves to the antibody. The reduced fluorescence on the tip 42 is sensed by the light sensing means. The relative decrease in fluorescence can be extrapolated into a relative quantity of drug molecules in the airstream directed through chamber 20. The free drug will replace the derivatized drug on the antibody for one of two reasons: (1) the structure of the drug molecule is altered during derivatization and is not bound as tightly to the antibody as would be the free drug, or (2) replacement occurs due to simple equilibrium considerations.

Figure 3:
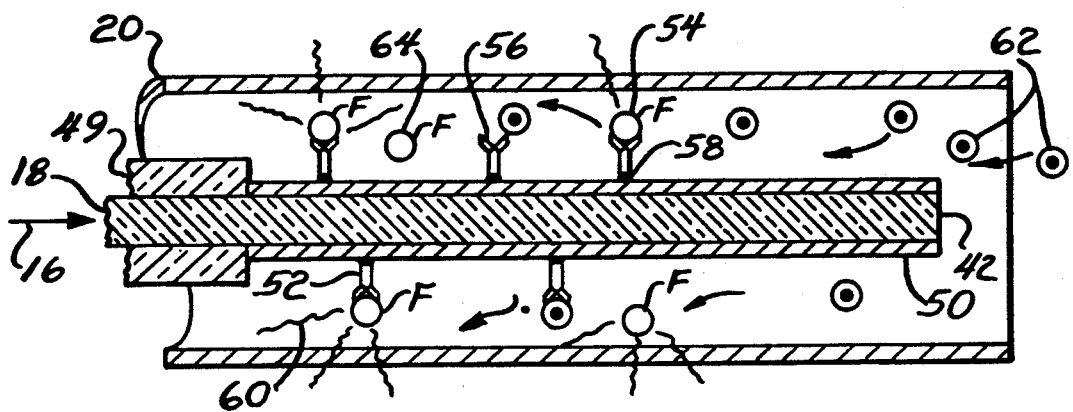
FIG. 3 is an enlarged drawing of the drug sensor tip.

FIG. 3 illustrates an enlarged section of the optical fiber 18 having a jacket 49 and the distal tip 42 with the protein coating 50. Antibodies 52 are attached to the coating 50, and derivatized antigens 54 are illustrated attached to the specific "front end" ($F_{ab}$ region) site 56 on the antibody 52. The opposite end ($F_c$ region) 58 attaches the antibody 52 to the coating 50. As the light beam 16, filtered at the excitation wavelength, passes into the distal tip 42 of fiber 18, it causes fluorescence 60 of the tagged antigens 54 that can be monitored by a spectroscope.

Drug molecules 62, having an affinity for the antibody 52, displace fluorescently-tagged antigen 54, illustrated at 64, causing reduced fluorescence at distal tip 42.

Figure 4:
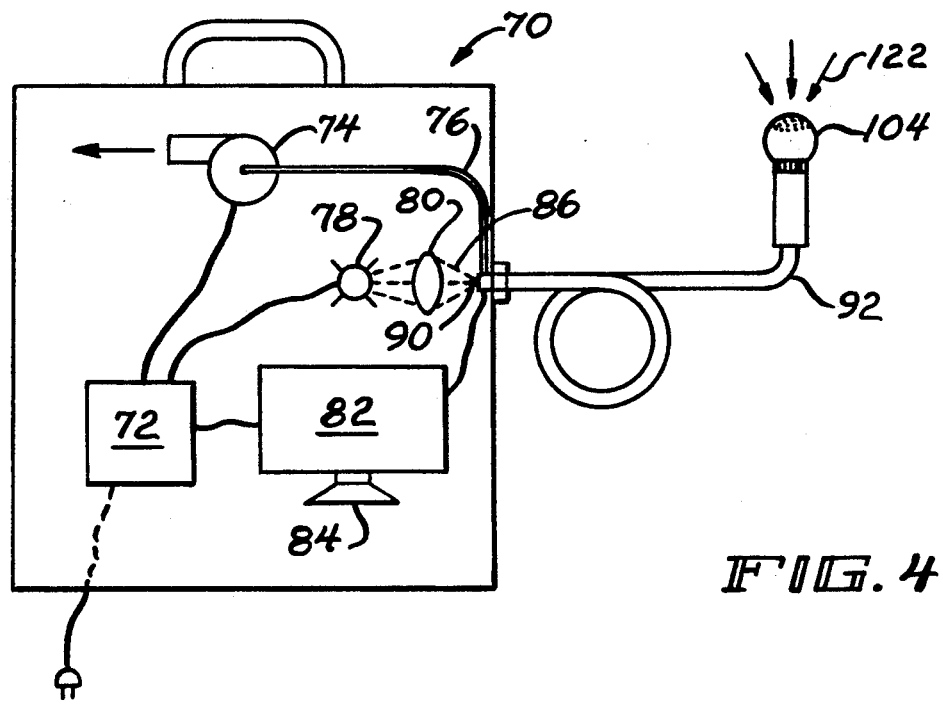
FIG. 4 is a diagrammatic view of the apparatus of the present invention.
Figure 5:
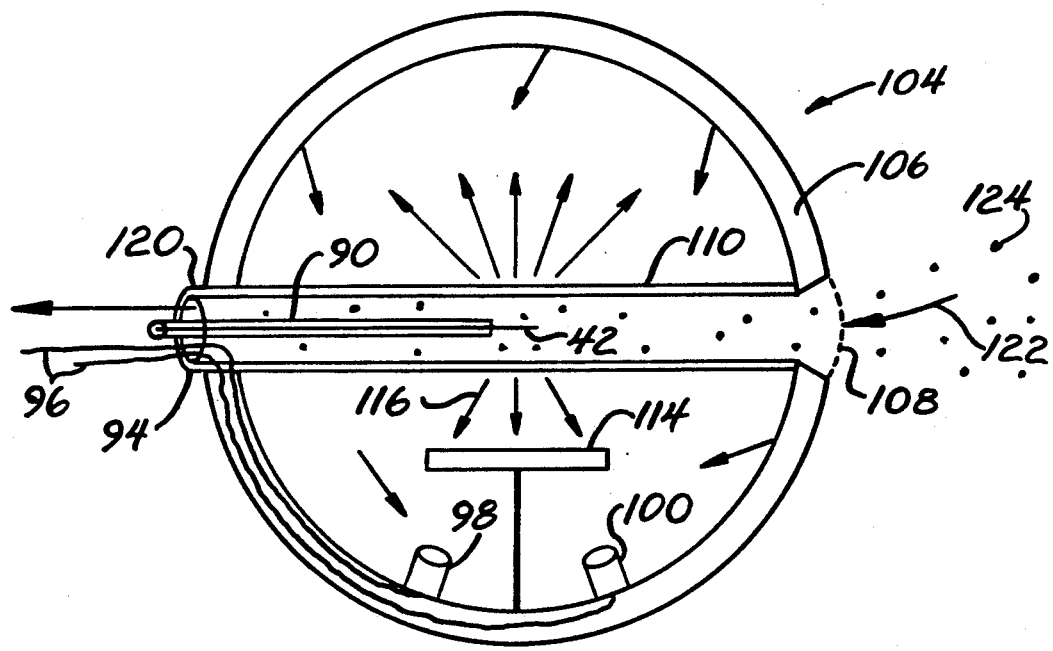
FIG. 5 is a schematic section view of the sensor head.

A preferred embodiment of the apparatus of the present invention is illustrated in FIGS. 4 and 5. Case 70 contains a power supply 72, vacuum pump 74, vacuum connection 76, filtered light source 78, focusing lens 80, electronics package 82 and alarm means 84. Filtered light 86 is focused into the end of an optical fiber 90 which is contained within flexible cable 92. Also contained within cable 92 is a vacuum line 94 and electrical conductors 96 that connect the photodiodes 98 and 100 to the electronics package 82.

Sensor assembly 104 comprises an internally reflective integrating chamber or sphere 106 having an air entry aperture 108. A glass tube 110 contains the coated optical fiber 90, with the fluorescent fiber optic tip 42 located approximately at the midpoint of the sphere 106. Light baffle 114 is installed between optic tip 42 and photodiodes 98, 100 to prevent direct photon 116 impingement onto the diodes so that an integrated light measurement may be achieved. The two diodes comprise a detector photodiode 98 and a reference photodiode 100, the latter used as a comparator to detect a general change in light intensity due to variables such as interferring compounds, power supply voltage changes, light leaks, etc.

In operation, vacuum pump 74 is actuated, thereby drawing ambient air 120 into the integrating sphere 106, as at 108, to exit the sphere at exit aperture 120. As the air sample passes through tube 110, if there are drug molecules 124 present, they will displace the tagged antigen contained on the fiber tip 42, thereby reducing fluorescence and photon 116 impingement on diodes 98, 100. Reduced light perceived by photodiode 98 is translated to a reduced electrical output into the electronic package 82, thereby activating alarm means 84 at a pre-calibrated voltage level.

The tip portion 42 of optical fiber 90 may be attached to the fiber by a coupling which permits replacement of the tip after sufficient use that its fluorescent properties are diminished.

It is to be understood that while the present application discloses the invention in the context of drug detection, the invention is equally applicable for use with any molecular compound that: (1) can be used to produce antibodies and (2) has a reactive site to which a fluorescent compound can be affixed and which will be displaced from an antibody by the compound of interest. For example, many industrial hazardous chemicals, many pesticides, and many chemical and biological warfare agents can be detected using the method and apparatus of the present invention. In addition, drugs other than heroin and cocaine can be detected by this process, such as marijuana (the active chemical being tetrahydrocannabinol).

While a preferred embodiment of the invention has been disclosed, various modes of carrying out the principles disclosed herein are contemplated as being within the scope of the following claims. Therefore, it is understood that the scope of the invention is not to be limited except as otherwise set forth in the claims.

We claim:
1. A fiber optic detector apparatus for use in detecting specific molecular compounds in air, comprising:
   a. a chamber containing at least one photon sensing device;
   b. a clear tube within the chamber having an entry aperture and an exit aperture;
   c. an optical fiber within said clear tube, at least a portion of said fiber having adhered thereto a quantity of antibodies specific for said molecular compound, and antigens affixed to the antibodies having a fluorescent compound affixed thereto;
   d. air evacuation means connected to the exit aperture; which draws gas from the entry aperture to the exit aperture;
   e. a filtered light source directing light into the optical fiber; and
   f. an electronic package connected to the photon sensing device comprising power supply and alarm means, such that when a change in fluorescence is detected by the photon sensing device, the alarm means is activated.

2. The apparatus as recited in claim 1, wherein the photon sensing device comprises a detector photodiode and a reference photodiode.

3. The apparatus as recited in claim 1, wherein the chamber is a sphere having a reflecting inner surface.

4. The apparatus as recited in claim 1, wherein said antibodies are adhered to the optical fiber by applying to the optical fiber a chemical reagent selected from the group consisting of 3-aminopropyltrimethoxysilane, 3-aminopropyltriethyoxysilane, and 3-carboxypropyltrimethoxysilane and then a protein.

5. The apparatus as recited in claim 1, wherein the specific molecular compound comprises a drug selected from the group consisting of heroin, cocaine and tetrahydrocannabinol.

6. The apparatus as recited in claim 1, wherein the fluorescent compound is selected from the group consisting of fluorescein and rhodamine.

7. A fiber optic detector apparatus for use in detecting illegal drugs in air, comprising:
   a. a chamber containing at least one photon sensing device; which draws gas from the entry aperture to the exit aperture;
   b. a clear tube within the chamber having an entry aperture and an exit aperture;
   c. an optical fiber within said clear tube having a quantity of antibodies adhered thereto, said antibodies specific to the illegal drug to be detected;
   d. fluorescently-tagged antigens affixed to the antibodies;
   e. vacuum means connected to the exit aperture;
   f. a filtered light source directing light into the optical fiber;
   g. an electronic package connected to the photon sensing device comprising power supply and alarm means, such that when a change in fluorescence is detected by the photon sensing device, the alarm means is activated.

8. The apparatus as recited in claim 7, wherein the photon sensing device comprises a detector photodiode and a reference photodiode.

9. The apparatus as recited in claim 1, wherein the chamber is a sphere having a reflecting inner surface.

10. The apparatus as recited in claim 7, wherein the antibodies are adhered to the optic fiber with a chemical reagent selected from the group consisting of 3-aminopropyltrimethoxysilane, 3-aminopropyltriethyloxysilane and 3-carboxypropyltrimethoxysilane, and thereafter applying Protein A from *Staphylococcus aureus*.

11. The apparatus as recited in claim 10, wherein the chemical reagent is 3-aminopropyltrimethyoxysilane and the fluorescently-tagged antigen is tagged with fluorescein.

12. The apparatus as recited in claim 7, wherein the drugs detected are selected from the group comprising cocaine, heroin and tetrahydrocannabinol.

13. The apparatus as recited in claim 7, wherein the sphere further comprises a baffle to prevent direct impingement onto the photon sensing device of the fluorescent light from the optical fiber.

14. The apparatus as recited in claim 11, wherein the electronic package comprises a power supply, a light source, a focusing lens, vacuum means, and connections to the clear tube.

* * * * *